(12) United States Patent
Foo et al.

(10) Patent No.: US 7,709,673 B2
(45) Date of Patent: May 4, 2010

(54) PROCESS FOR MAKING 3-PENTENENITRILE BY HYDROCYANATION OF BUTADIENE

(75) Inventors: Thomas Foo, Wilmington, DE (US); Sigridur S. Kristjansdottir, Wilmington, DE (US); Ronald J. McKinney, Wilmington, DE (US); Ron Ozer, Wilmington, DE (US)

(73) Assignee: Invista North America S.A R.L., Wilmington, DE (US)

( * ) Notice: Subject to any disclaimer, the term of this patent is extended or adjusted under 35 U.S.C. 154(b) by 101 days.

(21) Appl. No.: 11/776,922

(22) Filed: Jul. 12, 2007

(65) Prior Publication Data

US 2008/0015378 A1    Jan. 17, 2008

Related U.S. Application Data

(60) Provisional application No. 60/830,869, filed on Jul. 14, 2006.

(51) Int. Cl.
C07C 253/00    (2006.01)

(52) U.S. Cl. .................................................. 558/332

(58) Field of Classification Search .................. 558/332
See application file for complete search history.

(56) References Cited

U.S. PATENT DOCUMENTS

| | | | |
|---|---|---|---|
| 3,496,215 | A | 2/1970 | Drinkard et al. |
| 3,536,748 | A | 10/1970 | Drinkard et al. |
| 3,655,723 | A | 4/1972 | Drinkard |
| 3,903,120 | A | 9/1975 | Shook, Jr. et al. |
| 4,298,546 | A | 11/1981 | McGill |
| 5,512,695 | A | 4/1996 | Kreutzer et al. |
| 5,512,696 | A | 4/1996 | Kreutzer et al. |
| 5,523,453 | A | 6/1996 | Breikss |
| 5,663,369 | A | 9/1997 | Kreutzer et al. |
| 5,688,986 | A | 11/1997 | Tam et al. |
| 5,693,843 | A | 12/1997 | Breikss et al. |

(Continued)

FOREIGN PATENT DOCUMENTS

| | | |
|---|---|---|
| WO | WO96/22968 | 8/1996 |
| WO | WO99/06355 | 2/1999 |
| WO | WO99/06357 | 2/1999 |
| WO | WO99/52632 | 10/1999 |

*Primary Examiner*—Rei-tsang Shiao
(74) *Attorney, Agent, or Firm*—Robert B. Furr, Jr.; Edward F. Kenehan, Jr.

(57) ABSTRACT

The invention provides a continuous process for the production of 3-pentenenitrile comprising:
(a) contacting, in a reaction zone, a hydrogen cyanide-containing feed, a butadiene-containing feed, and a catalyst precursor composition, wherein the catalyst precursor composition comprises a zero-valent nickel and at least one bidentate phosphite ligand selected from a member of the group represented by Structures I and II, in which all like reference characters have the same meaning, except as further explicitly limited:

Structure I

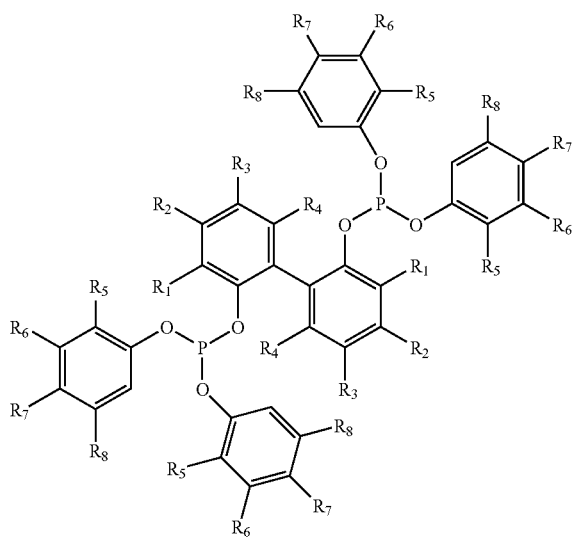

Structure II

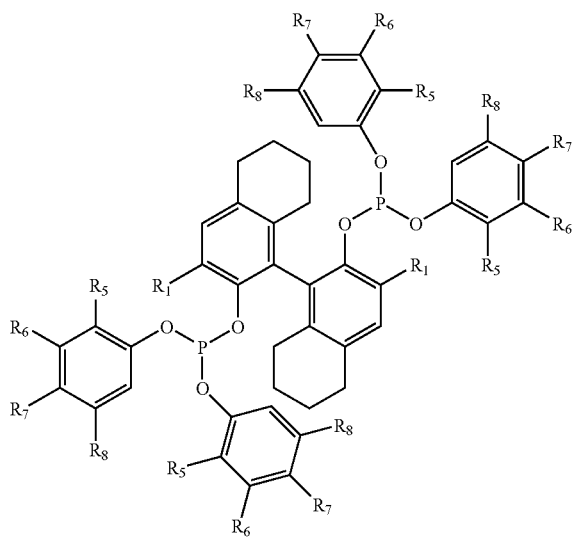

wherein $R_1$ and $R_5$ are independently selected from the group consisting of $C_1$ to $C_5$ hydrocarbyl, and $R_2$, $R_3$, $R_4$, $R_6$, $R_7$ and $R_8$ are independently selected from the group consisting of H and $C_1$ to $C_4$ hydrocarbyl; and (b) maintaining a residence time in the reaction zone sufficient to convert about 95% or more of the hydrogen cyanide and to produce a reaction mixture comprising 3-pentenenitrile and 2-methyl-3-butenenitrile, wherein the 2-methyl-3-butenenitrile concentration is maintained below about 15 weight percent of the total mass of the reaction mixture.

14 Claims, No Drawings

U.S. PATENT DOCUMENTS

| | | |
|---|---|---|
| 5,723,641 A | 3/1998 | Tam et al. |
| 5,821,378 A | 10/1998 | Foo et al. |
| 5,959,135 A | 9/1999 | Garner et al. |
| 5,981,722 A | 11/1999 | Chen et al. |
| 6,020,516 A | 2/2000 | Foo et al. |
| 6,069,267 A | 5/2000 | Tam |
| 6,127,567 A | 10/2000 | Garner et al. |
| 6,169,198 B1 | 1/2001 | Fischer et al. |
| 6,171,996 B1 | 1/2001 | Garner et al. |
| 6,171,997 B1 | 1/2001 | Foo et al. |
| 6,893,996 B2 | 5/2005 | Chu et al. |
| 6,936,171 B2 | 8/2005 | Jackson et al. |
| 2003/0100802 A1 | 5/2003 | Shapiro |
| 2004/0106815 A1 | 6/2004 | Ritter |
| 2004/0176622 A1* | 9/2004 | Bartsch et al. ............ 556/16 |

* cited by examiner

PROCESS FOR MAKING 3-PENTENENITRILE BY HYDROCYANATION OF BUTADIENE

CROSS-REFERENCE TO RELATED APPLICATIONS

This application claims benefit of priority from Provisional Application No. 60/830,869, filed Jul. 14, 2006. This application hereby incorporates by reference Provisional Application No. 60/830,869 in its entirety. This application relates to commonly-assigned applications filed concurrently on Jul. 12, 2007 as Ser. Nos. 11/776,904, 11/776,932, 11/776,954 and 11/776,968.

FIELD OF THE INVENTION

The invention relates to the hydrocyanation of 1,3-butadiene to produce 3-pentenenitriles and other unsaturated nitrites. More particularly, this invention relates to a process for the hydrocyanation of 1,3-butadiene using a catalyst precursor composition comprising a zero-valent nickel and at least one bidentate phosphite ligand.

BACKGROUND OF THE INVENTION

3-Pentenenitrile (3PN) is an important intermediate in the production of adiponitrile (ADN). ADN is of particular interest because it is a commercially versatile and important intermediate in the industrial production of nylon polyamides useful in forming films, fibers, and molded articles.

It is well known in the art that 3PN may be formed through a series of reactions as illustrated in Equations 1 and 2 below,

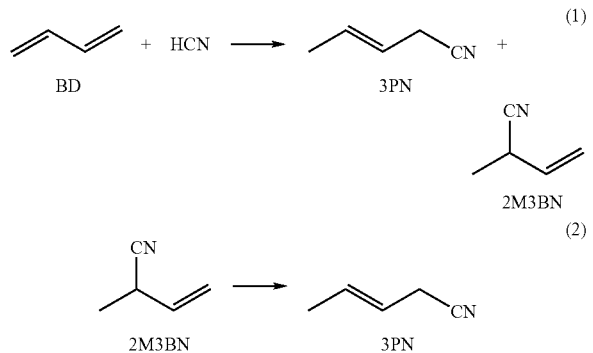

wherein BD is butadiene, HCN is hydrogen cyanide, and 2M3BN is the BD hydrocyanation co-product 2-methyl-3-butenenitrile. U.S. Pat. No. 3,496,215 describes the catalytic hydrocyanation of BD (equation 1) in the presence of $NiL_4$ complexes wherein L is a monodentate phosphorus-containing ligand. The relative amounts of 3PN and 2M3BN can be dependent upon the catalyst utilized in this chemical reaction. U.S. Pat. No. 3,536,748 describes the catalytic isomerization of 2M3BN to 3PN (equation 2) in the presence of $NiL_4$ complexes.

U.S. Pat. No. 3,536,748 discloses that in the presence of HCN, the nickel complex preferentially catalyzes formation of undesired, six-carbon, saturated dinitrile (2-methylglutaronitrile, MGN) from 2M3BN (see Equation 3 below). This patent notes that, because of the overriding competitive hydrocyanation reaction, for the isomerization of 2M3BN to 3PN it is necessary to avoid the presence of large amounts of HCN, for example any amount of the order of or in excess of 1:1 mole ratio with the 2M3BN starting material. The reference further discloses that HCN has no significant effect per se on the isomerization reaction, its presence in minor amounts in the starting material can be tolerated if necessary, and the isomerization process is preferably conducted in the absence of HCN.

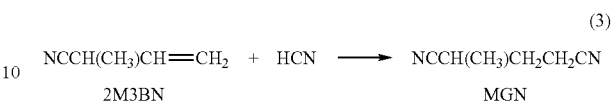

U.S. Pat. No. 6,169,198 discloses that hydrocyanation of BD to prepare ADN can generally be divided into three steps. The first is synthesis of mononitriles by hydrocyanation of BD (as in Equation 1 above), for which the selectivity for the linear 3PN is about 70% or less, depending on the catalyst used. The second is isomerization of the 2M3BN present in the mixtures to 3PN (as in Equation 2 above) and isomerization of 3PN to various n-pentenenitriles; the third is synthesis of dinitriles. Also disclosed is a preferred embodiment in which the ratio of the amounts of 3PN to 2M3BN obtained in the monoaddition of HCN onto the BD-containing hydrocarbon mixture is at least 5:1, preferably at least 10:1, in particular at least 20:1, with a catalyst comprising at least one metallocene-phosphorus(III)-nickel(0) complex. The reference further discloses that it is generally possible to dispense with division of the process for preparing ADN into the three steps of monoaddition of HCN onto a BD-containing hydrocarbon mixture; isomerization; addition of hydrogen cyanide onto 4-pentenenitrile (4PN) formed in situ; and the addition of 2 mole equivalents of HCN onto a BD-containing hydrocarbon mixture can be designed as a one-stage process.

In recent years, a new class of catalysts has been described for the transformations of Equations 1 and 2. U.S. Pat. Nos. 5,512,695; 5,512,696; 5,523,453; 5,663,369; 5,688,986; 5,693,843; 5,723,641; 5,821,378; 5,959,135; 5,981,772; 6,020,516; 6,127,567; 6,171,996; 6,171,997; and WO99/52632 describe the use of diphosphite and diphosphinite nickel complexes as catalysts for the hydrocyanation of BD or 3PN and the isomerization of 2M3BN to 3PN. In general, this class of catalysts is characterized by greater catalytic activity and resistance to HCN-derived degradation reactions compared to the catalysts comprising nickel complexes of monodentate phosphites and phosphinites. As a result, this new class of catalysts may generally be used effectively at much lower concentrations and over a broader range of reaction conditions. U.S. Pat. Nos. 5,821,378; 5,981,772 and 6,020,516 describe the capability of a limited number of these catalyst systems to isomerize 2M3BN at the same temperature at which BD is hydrocyanated.

It would be desirable to have a high yield 3PN process in which BD hydrocyanation and 2M3BN isomerization occur concurrently in the same reaction zone. Such a combined BD hydrocyanation/2M3BN isomerization process would have fewer reaction and process separation steps than a process in which the hydrocyanation and isomerization reactions were performed, for example, in separate reaction zones under reaction conditions optimized independently for BD hydrocyanation or for 2M3BN isomerization to 3PN. The advantages of a combined BD hydrocyanation/2M3BN isomerization process having simplified process complexity could include reduced capital investment and reduced cost of manufacture. Reduced yield loss to undesired by-products, such as MGN and compounds derived from butadiene dimerization and/or oligomerization, might also be realized with a combined BD hydrocyanation/2M3BN isomerization process.

SUMMARY OF THE INVENTION

In a first aspect, the present invention can provide a process for the continuous production of 3-pentenenitrile, comprising: (a) contacting, in a reaction zone, a hydrogen cyanide (HCN)-containing feed, a butadiene (BD)-containing feed, and a catalyst precursor composition, wherein the catalyst precursor composition comprises a zero-valent nickel and at least one bidentate phosphite ligand selected from a member of the group represented by Structures I and II in which all like reference characters have the same meaning, except as further explicitly limited:

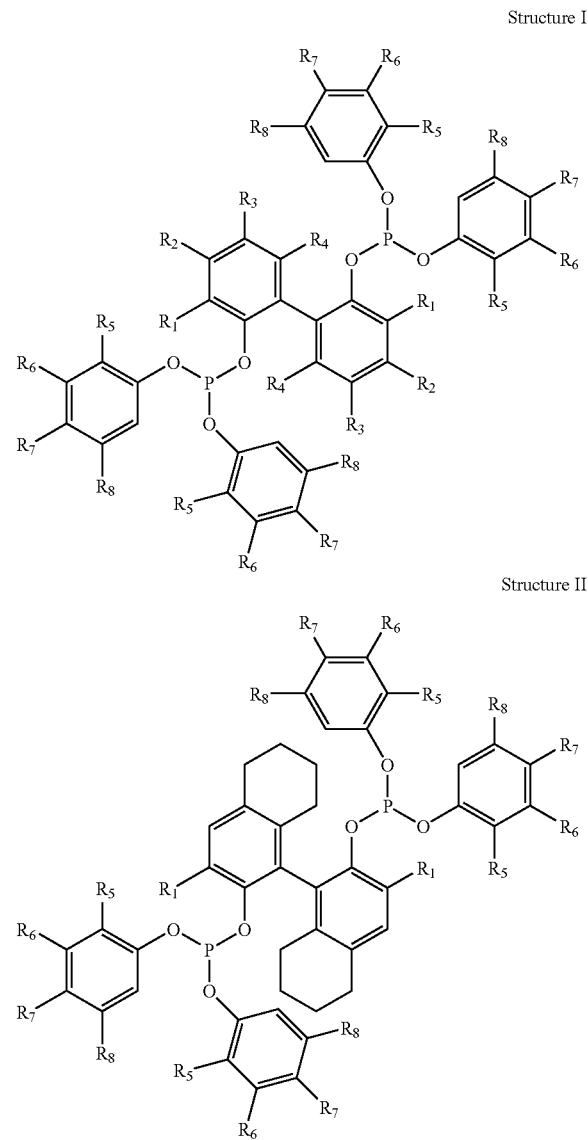

Structure I

Structure II wherein $R_1$ and $R_5$ are independently selected from the group consisting of $C_1$ to $C_5$ hydrocarbyl, and $R_2$, $R_3$, $R_4$, $R_6$, $R_7$ and $R_8$ are independently selected from the group consisting of H and $C_1$ to $C_4$ hydrocarbyl; and (b) maintaining a residence time in the reaction zone sufficient to convert about 95% or more of the hydrogen cyanide and to produce a reaction mixture comprising 3-pentenenitrile and 2-methyl-3-butenenitrile, wherein the 2-methyl-3-butenenitrile concentration is maintained below about 15 weight percent of the total mass of the reaction mixture.

Another aspect of the present invention is the process wherein the molar ratio of the hydrogen cyanide in the feed to the butadiene in the feed is in the range of about 0.90:1.00 to about 1.04:1.00, and the molar ratio of the zero-valent nickel in the feed to the butadiene in the feed is in the range of about 0.00005:1.00 to about 0.0050:1.00.

Another aspect of the present invention is the process wherein the temperature is maintained within a range of about 80° C. to about 140° C.

Another aspect of the present invention is the process wherein the catalyst precursor composition further comprises at least one monodentate phosphite ligand.

Another aspect of the present invention is the process wherein the bidentate phosphite ligand is selected from a member of the group represented by Structures I and II wherein $R_1$ is methyl, ethyl, isopropyl or cyclopentyl; $R_2$ is H or methyl; $R_3$ is H or a $C_1$ to $C_4$ hydrocarbyl; $R_4$ is H or methyl; $R_5$ is methyl, ethyl or isopropyl; and $R_6$, $R_7$ and $R_8$ are independently selected from the group consisting of H and $C_1$ to $C_4$ hydrocarbyl.

Another aspect of the present invention is the process wherein the bidentate phosphite ligand is selected from a member of the group represented by Structure I, wherein $R_1$, $R_4$, and $R_5$ are methyl; $R_2$, $R_6$, $R_7$ and $R_8$ are H; and $R_3$ is a $C_1$ to $C_4$ hydrocarbyl.

Another aspect of the present invention is the process wherein the bidentate phosphite ligand is selected from a member of the group represented by Structure I, wherein $R_1$ is isopropyl; $R_2$ is H; $R_3$ is a $C_1$ to $C_4$ hydrocarbyl; $R_4$ is H or methyl; $R_5$ is methyl or ethyl; $R_6$ and $R_8$ are H or methyl; and $R_7$ is H, methyl or tertiary-butyl.

Another aspect of the present invention is the process wherein the bidentate phosphite ligand is selected from a member of the group represented by Structure II wherein $R_1$ is isopropyl or cyclopentyl; $R_5$ is methyl or isopropyl; and $R_6$, $R_7$, and $R_8$ are H.

Another aspect of the present invention is the process wherein the bidentate phosphite ligand is represented by Structure I, wherein $R_1$ is isopropyl; $R_2$, $R_6$, and $R_8$ are H; and $R_3$, $R_4$, $R_5$, and $R_7$ are methyl.

Another aspect of the present invention is the process wherein the temperature is maintained within the range of about 100° C. to about 130° C.

Another aspect of the present invention is the process wherein the molar ratio of the hydrogen cyanide in the feed to the butadiene in the feed is in the range of about 0.92:1.00 to about 0.98:1.00.

Another aspect of the present invention is the process wherein the molar ratio of the zero-valent nickel in the feed to the butadiene in the feed is in the range of about 0.0001:1.00 to about 0.0010:1.00.

Another aspect of the present invention is the process wherein the residence time is sufficient to maintain the 2-methyl-3-butenenitrile concentration at or below about 10 weight percent of the total mass of the reaction mixture.

Another aspect of the present invention is the process further comprising optionally contacting a feed comprising 2-methyl-3-butenenitrile in the reaction zone.

DETAILED DESCRIPTION OF THE INVENTION

The invention provides a process for the continuous production of 3PN in which a HCN-containing feed, a BD-containing feed, and a catalyst precursor composition solution are contacted, for example concurrently, in a reaction zone, for example a continuous-stirred-tank-reactor (CSTR), and a residence time in the reaction zone is maintained sufficient to convert about 95% or more of the HCN and to produce a reaction mixture comprising 3PN and 2M3BN, wherein the 2M3BN concentration is maintained below about 15 weight percent of the total mass of the reaction mixture.

In another aspect, the process of the invention further comprises optionally contacting a feed comprising 2M3BN in the reaction zone. The 2M3BN in the feed can be produced by a different process or prepared in a separate manufacturing facility. Alternatively, the 2M3BN in the feed may be obtained from a BD hydrocyanation and/or 2M3BN isomerization process as described in the art or the process of the current invention wherein a stream comprising 2M3BN may be, for example, distilled from a higher boiling reaction product comprising 3PN. Such a stream comprising 2M3BN can be recycled to the reaction zone of the present invention in which BD hydrocyanation and 2M3BN isomerization occurs. Potential advantages of such a process can include the elimination of investment and of the associated variable and fixed costs for operating an additional 2M3BN isomerization reaction vessel, distillation columns, and the associated pumps, heat exchangers, piping, and control instrumentation.

In processes falling within the scope of the present invention, the hydrocyanation and isomerization reactions of Equations 1 and 2 (above) can be carried out concurrently and continuously in the same reaction zone, for example under high BD and HCN conversion conditions.

The catalyst precursor composition comprises a zero-valent nickel and at least one bidentate phosphite ligand selected from a member of the group represented by Structures I and II, in which all like reference characters have the same meaning, except as further explicitly limited:

Structure I

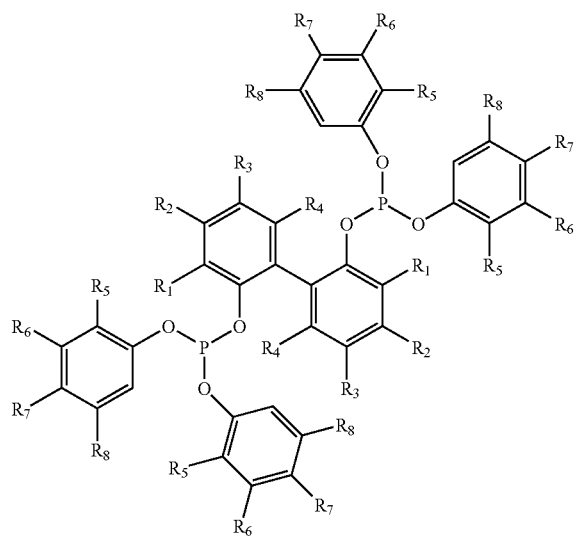

-continued

Structure II

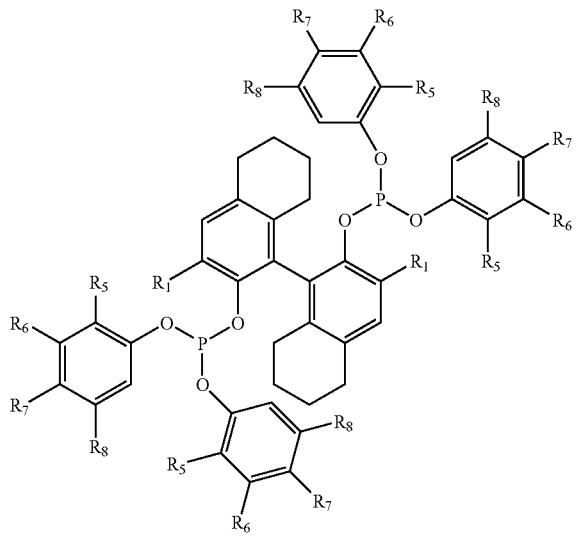

wherein $R_1$ and $R_5$ are independently selected from the group consisting of $C_1$ to $C_5$ hydrocarbyl, and $R_2$, $R_3$, $R_4$, $R_6$, $R_7$ and $R_8$ are independently selected from the group consisting of H and $C_1$ to $C_4$ hydrocarbyl.

It will be recognized that Structure I and Structure II are two-dimensional representations of three-dimensional molecules and that rotation about chemical bonds can occur in the molecules to give configurations differing from those shown. For example, rotation about the carbon-carbon bond between the 2- and 2'-positions of the biphenyl and octahydrobinaphthyl bridging groups of Structure I and Structure II respectively, can bring the two phosphorus atoms of each Structure in closer proximity to one another and can allow the phosphite ligand to bind to nickel in a bidentate fashion. The term "bidentate" is well known in the art and means both phosphorus atoms of the ligand are bonded to a single nickel atom.

The term "hydrocarbyl" is well known in the art and designates a hydrocarbon molecule from which at least one hydrogen atom has been removed. Such molecules can contain single, double, or triple bonds.

The term "aryl" is well known in the art and designates an aromatic hydrocarbon molecule from which at least one hydrogen atom has been removed.

Examples of suitable aryl groups include those containing 6 to 10 carbon atoms, which can be unsubstituted or singly or multiply substituted. Suitable substituents include, for example, $C_1$-$C_4$ hydrocarbyl, or halogen such as fluorine, chlorine or bromine, or halogenated hydrocarbyl such a trifluoromethyl, or aryl such as phenyl.

Each catalyst precursor composition useful in the present invention may be considered a "precursor" composition in that the zero-valent nickel at some point becomes bound to a bidentate phosphite ligand, and further in all likelihood, additional reactions occur during hydrocyanation, such as, for example, complexing of the initial catalyst composition to an ethylenically unsaturated compound.

As used herein, the term "catalyst precursor composition" also includes within its meaning recycled catalyst, that is, a catalyst precursor composition comprising a zero-valent nickel and at least one bidentate phosphite ligand which, having been used in the process of the invention, is returned or may be returned to the process and used again.

The catalyst precursor compositions may further comprise at least one monodentate phosphite ligand, provided that the monodentate phosphite ligand does not detract from the beneficial aspects of the invention. The monodentate phosphite ligand may be present as an impurity from synthesis of the bidentate phosphite ligand, or the monodentate phosphite ligand may be added as an additional component of the catalyst precursor composition.

The bidentate phosphite ligand is selected from a member of the group represented by Structures I and II in which all like reference characters have the same meaning, except as further explicitly limited:

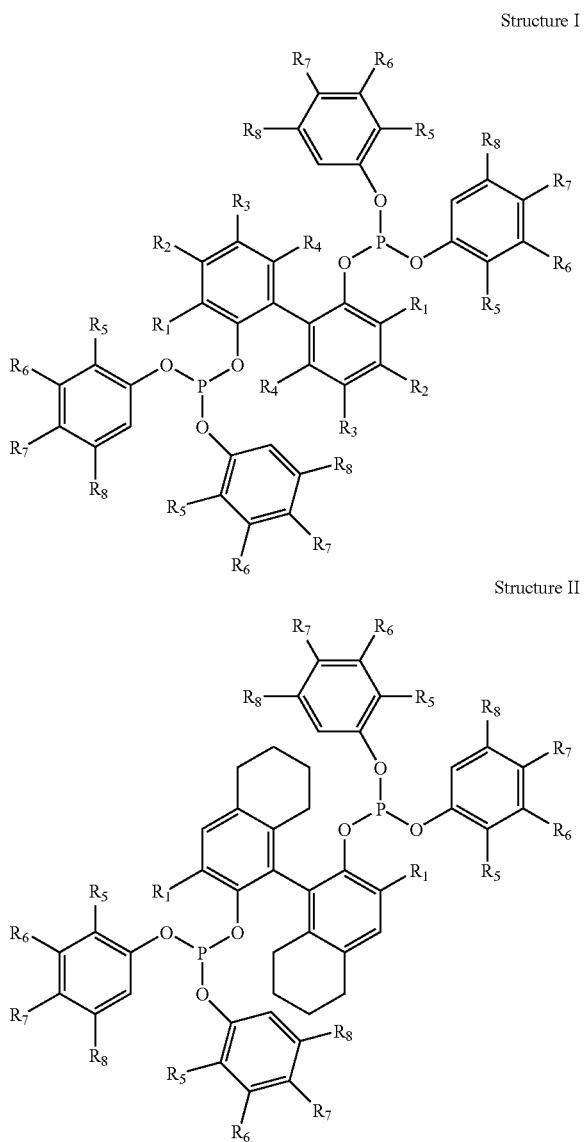

Structure I

Structure II wherein $R_1$ and $R_5$ are independently selected from the group consisting of $C_1$ to $C_5$ hydrocarbyl, and $R_2$, $R_3$, $R_4$, $R_6$, $R_7$ and $R_8$ are independently selected from the group consisting of H and $C_1$ to $C_4$ hydrocarbyl.

For example, the bidentate phosphite ligand can be selected from a member of the group represented by Structures I and II wherein $R_1$ is methyl, ethyl, isopropyl or cyclopentyl;
$R_2$ is H or methyl;
$R_3$ is H or a $C_1$ to $C_4$ hydrocarbyl;
$R_4$ is H or methyl;
$R_5$ is methyl, ethyl or isopropyl; and
$R_6$, $R_7$ and $R_8$ are independently selected from the group consisting of H and $C_1$ to $C_4$ hydrocarbyl.

As additional examples, the bidentate phosphite ligand can be selected from a member of the group represented by Structure I, wherein $R_1$, $R_4$, and $R_5$ are methyl;
$R_2$, $R_6$, $R_7$ and $R_8$ are H; and
$R_3$ is a $C_1$ to $C_4$ hydrocarbyl;
or
$R_1$ is isopropyl;
$R_2$ is H;
$R_3$ is a $C_1$ to $C_4$ hydrocarbyl;
$R_4$ is H or methyl;
$R_5$ is methyl or ethyl;
$R_6$ and $R_8$ are H or methyl; and
$R_7$ is H, methyl or tertiary-butyl;

or the bidentate phosphite ligand can be selected from a member of the group represented by Structure II, wherein $R_1$ is isopropyl or cyclopentyl;
$R_5$ is methyl or isopropyl; and
$R_6$, $R_7$, and $R_8$ are H.

As yet another example, the bidentate phosphite ligand can be represented by Structure I, wherein $R_1$ is isopropyl; $R_2$, $R_6$, and $R_8$ are H; and $R_3$, $R_4$, $R_5$, and $R_7$ are methyl.

The bidentate phosphite ligands useful in the catalyst precursor compositions employed in the present invention may be prepared by any suitable synthetic means known in the art, for example as described in U.S. Pat. Nos. 6,171,996 and 5,512,696, both of which are incorporated herein by reference. For example, the reaction of two equivalents of an ortho-substituted phenol with phosphorus trichloride gives the corresponding phosphorochloridite. The reaction of the phosphorochloridite with the desired substituted biphenol or octahydrobinaphthol in the presence of triethylamine gives the bidentate phosphite ligand. The crude bidentate phosphite ligand can be worked up by the process described in U.S. Pat. No. 6,069,267, which is incorporated herein by reference. As disclosed therein, the bidentate phosphite ligand product mixture can typically contain the desired product in about 70% to about 90% selectivity, with other phosphite by-products such as monodentate phosphites making up the balance of the product mixture. The bidentate phosphite ligand itself or these bidentate/monodentate phosphite ligand mixtures are suitable for use with the present invention.

The catalyst precursor compositions employed for this process should ideally be substantially free of carbon monoxide, oxygen, and water and may be preformed or prepared in situ according to techniques well known in the art. The catalyst precursor composition may be formed by contacting the bidentate phosphite ligand with a zero-valent nickel compound having ligands easily displace by organophosphite ligands, such as $Ni(COD)_2$, $Ni[P(O-o-C_6H_4CH_3)_3]_3$, and $Ni[P(O-o-C_6H_4CH_3)_3]_2(C_2H_4)$, all of which are well known in the art, wherein 1,5-cyclooctadiene (COD), tris(ortho-tolyl)phosphite $[P(O-o-C_6H_4CH_3)_3]$, and ethylene $(C_2H_4)$ are the easily displaced ligands. Elemental nickel, preferably nickel powder, when combined with a halogenated catalyst, as described in U.S. Pat. No. 3,903,120, is also a suitable source of zero-valent nickel. Alternatively, divalent nickel compounds can be combined with a reducing agent, to serve as a source of zero-valent nickel in the reaction, in the presence of the bidentate phosphite ligands. Suitable divalent nickel compounds include compounds of the formula $NiZ_2$ where Z is halide, carboxylate, or acetylacetonate. Suitable reducing agents include metal borohydrides, metal aluminum hydrides, metal alkyls, Li, Na, K, Zn, Fe or $H_2$. See, for example, U.S. Pat. No. 6,893,996. In the catalyst precursor composition, the bidentate phosphite ligand may be present in excess of what can theoretically be coordinated to the nickel at a given time.

The catalyst precursor composition may be dissolved in a solvent that is non-reactive toward, and miscible with, the hydrocyanation reaction mixture. Suitable solvents include, for example, aliphatic and aromatic hydrocarbons with 1 to 10 carbon atoms, and nitrile solvents such as acetonitrile. Alternatively, 3PN, a mixture of isomeric pentenenitriles, a mixture of isomeric methylbutenenitriles, a mixture of isomeric pentenenitriles and isomeric methylbutenenitriles, or the reaction product from a previous reaction campaign, may be used to dissolve the catalyst precursor composition.

The reaction temperature is typically maintained within the range of about 80° C. to about 140° C. for example within the range of about 100° C. to about 130° C. Generally, the reaction pressure should be sufficient to maintain the reagents in the liquid state, with such pressure at least, in part, a function of the amount of unreacted BD present in the reaction mixture. Though the invention is not limited by an upper limit of pressure, for practical purposes the pressure generally ranges from about 15 psia to about 300 psia (about 103 kPa to about 2068 kPa).

HCN, substantially free of carbon monoxide, oxygen, ammonia, and water can be introduced to the reaction as a vapor, liquid, or mixtures thereof. As an alternative, a cyanohydrin can be used as the source of HCN. See, for example, U.S. Pat. No. 3,655,723.

The molar ratio of the HCN in the feed to the BD in the feed is in the range of about 0.90:1.00 to about 1.04:1.00, for example in the range of about 0.92:1.00 to about 0.98:1.00. This range of molar ratios can be advantageous over those with a significantly larger excess of BD to HCN in that there can be less unreacted BD to recover and recycle to the process, and yield losses to MGN and to BD dimers, oligomers, and related species can be reduced.

The molar ratio of the zero-valent nickel in the feed to the BD in the feed is in the range of about 0.00005:1.00 to about 0.0050:1.00, for example in the range about 0.0001:1.00 to about 0.0010:1.00.

The residence time in the reaction zone (for example, the time necessary for the combined feeds to displace one reactor volume in a CSTR) is typically determined by the desire to maintain the 2M3BN concentration below about 15 weight percent of the total mass of the reaction mixture, for example at or below about 10 weight percent of the total mass of the reaction mixture, and is also related to the catalyst concentration and reaction temperature. Generally residence times will be in the range of about 0.5 to about 15 hours, for example in the range of about 1 to about 10 hours.

The hydrocyanation and isomerization reaction mixture may be used "as is" in subsequent reaction steps for the production of ADN. Alternatively, the reaction product and components of the catalyst precursor composition can be recovered by conventional techniques known in the art, such as, for example, by liquid-liquid extraction as disclosed in U.S. Pat. No. 6,936,171 and by flash distillation, for example at a pressure in the range of about 10 torr to about 700 torr (about 1 kPa to about 93 kPa). The catalyst precursor composition-containing "distillation tails" may be recycled back to the reaction zone after purging a portion of the mixture to prevent build-up of "high boiling" impurities. The reaction product, the "distillation make", is a mixture comprised predominantly of 3PN, with lesser amounts of isomeric pentenenitriles, 2M3BN, 2-methyl-2-butenenitrile, BD, HCN, and vinylcyclohexene. The desired 3PN and other isomeric pentenenitriles can be recovered from the reaction product by distillation and other constituent parts such as BD, HCN, and 2M3BN either recycled to the reaction zone or disposed of.

The following Examples were performed using a catalyst precursor composition wherein the bidentate phosphite ligand, referred to as "Phosphite A" in the chemical formula for the nickel source below, is represented by Structure I wherein $R_1$ is isopropyl; $R_2$, $R_6$, and $R_8$ are H; and $R_3$, $R_4$, $R_5$, and $R_7$ are methyl. The nickel source charged to the autoclave comprised the compound (Phosphite A)Ni(crotyl)CN dissolved in a nitrile solvent mixture. "Crotyl" represents a butenyl group having the empirical formula $C_4H_7$.

Phosphite A of the Examples may be prepared by any suitable synthetic means known in the art. For example, 3,3'-diisopropyl-5,5',6,6'-tetramethyl-2,2'-biphenol can be prepared by the procedure disclosed in United States Published Patent Application No. 2003/0100802, which is incorporated herein by reference, in which 4-methylthymol can undergo oxidative coupling to the substituted biphenol in the presence of a copper chlorohydroxide-TMEDA complex (TMEDA is N,N,N',N'-tetramethylethylenediamine) and air.

The phosphorochloridite of 2,4-xylenol, $(C_8H_9O)_2PCl$ can be prepared, for example, by the procedure disclosed in United States Published Patent Application No. 2004/0106815, which is incorporated herein by reference. To form this phosphorochloridite selectively, anhydrous triethylamine and 2,4-xylenol can be added separately and concurrently in a controlled manner to $PCl_3$ dissolved in an appropriate solvent under temperature-controlled conditions.

The reaction of the phosphorochloridite with the 3,3'-diisopropyl-5,5',6,6'-tetramethyl-2,2'-biphenol to form the desired Phosphite A can be performed, for example, according to the method disclosed in U.S. Pat. No. 6,069,267, which is hereby incorporated by reference. The phosphorochloridite can be reacted with 3,3'-diisopropyl-5,5',6,6'-tetramethyl-2,2'-biphenol in the presence of an organic base to form Phosphite A, which can be isolated according to techniques well known in the art, as also described in U.S. Pat. No. 6,069,267.

For each Example, the (Phosphite A)Ni(crotyl)CN compound was prepared as follows. In a nitrogen atmosphere, Phosphite A, represented by Structure I wherein $R_1$ is isopropyl; $R_2$, $R_6$, and $R_8$ are H; and $R_3$, $R_4$, $R_5$, and $R_7$ are methyl, and $Ni(COD)_2$ (COD is 1,5-cyclooctadiene) were combined in a molar ratio of 1:1 in a flask. Trans-3-pentenenitrile (95 wt %, Aldrich), which had been previously dried over molecular sieves and degassed with nitrogen, was added to the same flask (about 200 mL for 10 g of Phosphite A) and the mixture was stirred until an orange homogeneous solution formed. All volatiles were removed under vacuum at ambient temperature to yield an orange powder. The powder was triturated with anhydrous acetonitrile to remove excess pentenenitriles and other impurities, and then all volatiles were again removed under vacuum to produce (Phosphite A)Ni(crotyl)CN as an orange solid.

Trans-3-pentenenitrile (95 wt %) produced from BD hydrocyanation, 2M3BN isomerization, and pentenenitrile hydrocyanation processes may be obtained commercially from the Sigma-Aldrich Chemical Company. This material contains trace amounts of 2M3BN also prepared from a BD hydrocyanation and/or 2M3BN isomerization process.

The purity of the BD feed was greater than 99%. Freshly prepared anhydrous, uninhibited, liquid HCN was utilized in all Examples.

Embodiments falling within the scope of the present invention may be further understood in view of the following non-limiting examples.

EXAMPLES

Example 1

The reaction was carried out in a 100 mL autoclave fitted with a magnetically driven stirrer and dip legs for the addition of feeds. The reactor was operated liquid full, which resulted in a working volume of 118 mL. The reaction temperature was maintained at 120° C. by means of a combination of electrical heating on the outside and passing coolant through an internal coil. Pressure in the reactor was controlled by a manual back-pressure regulator at 130 psia (896 kPa). The exit tube continuously fed a flash-distillation column, which operated under reduced pressure (100 torr; 13.3 kPa) to separate the reaction products from the catalyst.

A catalyst precursor composition solution comprised of (Phosphite A)Ni(crotyl)CN (2.5 wt %), 1.6 wt % Phosphite A, and 1.2 wt % Phosphite A oxides, 3PN (82 wt %), 2PN (0.9 wt %), 4PN (1.2 wt %), 2M3BN (1.4 wt %), 2-methyl-2-butenenitriles (2M2BN, 0.7 wt %), dimethylsuccinonitrile (1.0 wt %), MGN (3.5 wt %), and ADN (2.4 wt %), was fed continuously and concurrently with BD and HCN to the autoclave such that the molar ratio of Ni:HCN:BD fed was about 0.00046:0.963:1.0 and the total flow rates were such that the residence time in the reactor was about 3.4 hours. Flows were maintained for 24 hours in order to approach a steady state condition. Samples were periodically drawn from the line exiting the reactor and analyzed by both high-pressure liquid chromatography (HPLC) for catalyst and by gas chromatography (GC) for nitrile products and byproducts. The 2M3BN was analyzed at 6.6 wt % of the reaction mixture. 92.9% of the BD and 96.5% of the HCN fed to the autoclave was converted into useful products comprised of 2PN, 3PN, and 4PN, and 2M3BN. Of the total moles of BD converted, the selectivity to these useful products was 96.7%.

Example 2

The reaction was carried out in a 1 liter autoclave fitted with a magnetically driven stirrer and dip legs for the addition of feeds and removal of product. The product removal dip leg was adjusted to provide a working volume of 750 mL. The reaction temperature was maintained at 110° C. by means of a combination of electrical heating on the outside and passing coolant through an internal coil. Pressure in the reactor was controlled by a manual back-pressure regulator at 100 psia (689 kPa). The exit tube continuously fed a flash-distillation column, which operated under reduced pressure (300 torr; 40 kPa) to separate reaction products from the catalyst.

A catalyst precursor composition solution comprised of (Phosphite A)Ni(crotyl)CN (2.8 wt %), 2.1 wt % Phosphite A, and 1.4 wt % Phosphite A oxides, 3PN (83 wt %), 2PN (6.1 wt %), 4PN (0.8 wt %), 2M3BN (1.4 wt %), 2M2BN (0.9 wt %), dimethylsuccinonitrile (1.0 wt %), MGN (0.2 wt %), and ADN (1.7 wt %), was fed continuously and concurrently with BD and HCN to the autoclave such that the molar ratio of Ni:HCN:BD fed was about 0.00055:0.946:1.0 and the total flow rates were such that the residence time in the reactor was about 7.3 hours. Flows were maintained for 40 hours in order to approach a steady state condition. Samples were periodically drawn from the line exiting the reactor and analyzed by both HPLC for catalyst and by GC for nitrile products and byproducts. The 2M3BN was analyzed at 6.6 wt % of the reaction mixture. 91.1% of the BD and 96.3% of the HCN fed to the autoclave was converted into useful products comprised of 2PN, 3PN, 4PN, and 2M3BN. Of the total moles of BD converted, the selectivity to these useful products was 96.1%

Example 3

The reaction was carried out in a 1 liter autoclave fitted with a magnetically driven stirrer and dip legs for the addition of feeds and extraction of product. The product removal dip leg was adjusted to provide a working volume of 750 mL. The reaction temperature was maintained at 120° C. by means of a combination of electrical heating on the outside and passing coolant through an internal coil. Pressure in the reactor was controlled by a manual back-pressure regulator at 100 psia (689 kPa). The exit tube continuously fed a flash-distillation column, which operated under reduced pressure (300 torr; 40 kPa) to separate reaction products from the catalyst.

A catalyst precursor composition solution comprised of (Phosphite A)Ni(crotyl)CN (2.8 wt %), 2.1 wt % Phosphite A, and 1.4 wt % Phosphite A oxides, 3PN (83 wt %), 2PN (6.1 wt %), 4PN (0.8 wt %), 2M3BN (1.4 wt %), 2M2BN (0.9 wt %), dimethylsuccinonitrile (1.0 wt %), MGN (0.2 wt %), and ADN (1.7 wt %), was fed continuously and concurrently with BD and HCN to the autoclave such that the molar ratio of Ni:HCN:BD fed was about 0.00025:0.948:1.0 and the total flow rates were such that the residence time in the reactor was about 8.2 hours. Flows were maintained for 40 hours in order to approach a steady state condition. Samples were periodically drawn from the line exiting the reactor and analyzed by both HPLC for catalyst and by GC for nitrile products and byproducts. The 2M3BN was analyzed at 10.3 wt % of the reaction mixture. 90.9% of the BD and 95.9% of the HCN fed to the autoclave was converted into useful products comprised of 2PN, 3PN, 4PN, and 2M3BN. Of the total moles of BD converted, the selectivity to these useful products was 96.5%

Example 4

The reaction was carried out in a 1 liter autoclave fitted with a magnetically driven stirrer and dip legs for the addition of feeds and extraction of product. The product removal dip leg was adjusted to provide a working volume of 750 mL. The reaction temperature was maintained at 130° C. by means of a combination of electrical heating on the outside and passing coolant through an internal coil. Pressure in the reactor was controlled by a manual back-pressure regulator at 100 psia (689 kPa). The exit tube continuously fed a flash-distillation column, which operated under reduced pressure (300 torr; 40 kPa) to separate reaction products from the catalyst.

A catalyst precursor composition solution comprised of (Phosphite A)Ni(crotyl)CN (2.8 wt %), 2.1 wt % Phosphite A, and 1.4 wt % Phosphite A oxides, 3PN (83 wt %), 2PN (6.1 wt %), 4PN (0.8 wt %), 2M3BN (1.4 wt %), 2M2BN (0.9 wt %), dimethylsuccinonitrile (1.0 wt %), MGN (0.2 wt %), and ADN (1.7 wt %), was fed continuously and concurrently with BD and HCN to the autoclave such that the molar ratio of Ni:HCN:BD fed was about 0.00035:0.925:1.0 and the total flow rates were such that the residence time in the reactor was about 2.0 hours. Flows were maintained for 12 hours in order to approach a steady state condition. Samples were periodically drawn from the line exiting the reactor and analyzed by both HPLC for catalyst and by GC for nitrile products and byproducts. The 2M3BN was analyzed at 12.4 wt % of the reaction mixture. 89.1% of the BD and 96.3% of the HCN fed to the autoclave was converted into useful products comprised of 2PN, 3PN, 4PN, and 2M3BN. Of the total moles of BD converted, the selectivity to these useful products was 96.7%.

Although particular embodiments of the present invention have been described in the foregoing description, it will be understood by those skilled in the art that the invention is capable of numerous modifications, substitutions and rearrangements without departing from the spirit or essential attributes of the invention. Reference should be made to the appended claims, rather than to the foregoing specification, as indicating the scope of the invention.

What is claimed is:

1. A process for the continuous production of 3-pentenenitrile, comprising:
(a) continuously introducing feed comprising hydrogen cyanide, 1,3-butadiene, and a catalyst precursor composition in a reaction zone, wherein the molar ratio of the hydrogen cyanide in the feed to the 1,3-butadiene in the feed is in the range of about 0.90:1.00 to about 1.04:1.00, and, wherein the catalyst precursor composition comprises a zero-valent nickel and at least one bidentate phosphite selected from a member of the group represented by Structures I and II:

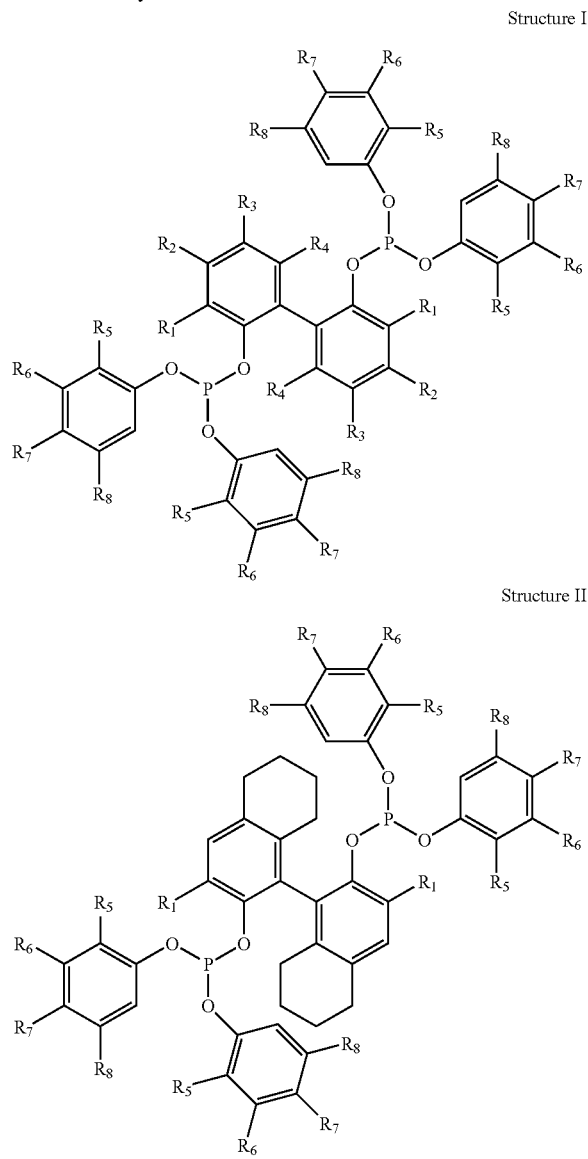

wherein $R_1$ and $R_5$ are independently selected from the group consisting of $C_1$ to $C_5$ hydrocarbyl, and $R_2$, $R_3$, $R_4$, $R_6$, $R_7$ and $R_8$ are independently selected from the group consisting of H and $C_1$ to $C_4$ hydrocarbyl;
(b) displacing a product mixture from the reaction zone by the feed which is continuously introduced into the reaction zone; and
(c) maintaining a residence time in the reaction zone sufficient to convert about 95% or more of the hydrogen cyanide and to produce the product mixture, wherein the product mixture comprises 3-pentenenitrile and 2-methyl-3-butenenitrile, and wherein the 2-methyl-3-butenenitrile concentration is maintained below about 15 weight percent of the total mass of the product mixture.

2. The process according to claim 1, wherein the molar ratio of the zero-valent nickel in the feed to the 1,3-butadiene in the feed is in the range of about 0.00005:1.00 to about 0.0050:1.00.

3. The process according to claim 1, wherein the temperature is maintained within a range of about 80° C. to about 140° C.

4. The process according to claim 1, wherein the bidentate phosphite ligand is selected from a member of the group represented by Structures I and II, wherein
$R_1$ is methyl, ethyl, isopropyl or cyclopentyl;
$R_2$ is H or methyl;
$R_3$ is H or a $C_1$ to $C_4$ hydrocarbyl;
$R_4$ is H or methyl;
$R_5$ is methyl, ethyl or isopropyl; and
$R_6$, $R_7$ and $R_8$ are independently selected from the group consisting of H and $C_1$ to $C_4$ hydrocarbyl.

5. The process according to claim 1, wherein the bidentate phosphite ligand is selected from a member of the group represented by Structure I, wherein
$R_1$, $R_4$, and $R_5$ are methyl;
$R_2$, $R_6$, $R_7$ and $R_8$ are H; and
$R_3$ is a $C_1$ to $C_4$ hydrocarbyl.

6. The process according to claim 1, wherein the bidentate phosphite ligand is selected from a member of the group represented by Structure I, wherein
$R_1$ is isopropyl;
$R_2$ is H;
$R_3$ is a $C_1$ to $C_4$ hydrocarbyl;
$R_4$ is H or methyl;
$R_5$ is methyl or ethyl;
$R_6$ and $R_8$ are H or methyl; and
$R_7$ is H, methyl or tertiary-butyl.

7. The process according to claim 1, wherein the bidentate phosphite ligand is selected from a member of the group represented by Structure II, wherein
$R_1$ is isopropyl or cyclopentyl;
$R_5$ is methyl or isopropyl; and
$R_6$, $R_7$, and $R_8$ are H.

8. The process according to claim 1, wherein the bidentate phosphite ligand is represented by Structure I, wherein
$R_1$ is isopropyl;
$R_2$, $R_6$, and $R_8$ are H; and
$R_3$, $R_4$, $R_5$, and $R_7$ are methyl.

9. The process according to claim 1, wherein the temperature is maintained within the range of about 100° C. to about 130° C.

10. The process according to claim 1, wherein the molar ratio of the hydrogen cyanide in the feed to the butadiene in the feed is in the range of about 0.92:1.00 to about 0.98:1.00.

11. The process according to claim 1, wherein the molar ratio of the zero-valent nickel in the feed to the butadiene in the feed is in the range of about 0.0001:1.00 to about 0.0010:1.00.

12. The process according to claim 1, wherein the residence time in the reaction zone is sufficient to maintain the 2-methyl-3-butenenitrile concentration at or below about 10 weight percent of the total mass of the product mixture.

13. The process according to claim 1, wherein said feed comprises 2-methyl-3-butenenitrile.

14. The process according to claim 1, wherein the catalyst precursor composition further comprises at least one monodentate phosphite ligand.

* * * * *